United States Patent [19]
Dodd-o et al.

[11] Patent Number: 6,090,851
[45] Date of Patent: Jul. 18, 2000

[54] USE OF AN NADPH-OXIDASE INHIBITOR IN THE TREATMENT OF REPERFUSION INJURY

[75] Inventors: Jeffrey M. Dodd-o, Baltimore; David B. Pearse, Ellicott City, both of Md.

[73] Assignee: Johns Hopkins University School of Medicine, Baltimore, Md.

[21] Appl. No.: 09/150,069

[22] Filed: Sep. 9, 1998

Related U.S. Application Data

[60] Provisional application No. 60/058,446, Sep. 10, 1997, and provisional application No. 60/071,188, Jan. 12, 1998.

[51] Int. Cl.[7] .......................... A61K 31/19; A61K 31/12; A61K 31/11; A61K 31/075; A61K 31/05
[52] U.S. Cl. .......................... 514/568; 514/689; 514/699; 514/717; 514/731
[58] Field of Search .................. 514/568, 689, 514/699, 717, 731

[56] References Cited

U.S. PATENT DOCUMENTS 5,763,496  6/1998  Holland ................... 514/689

FOREIGN PATENT DOCUMENTS 551662  7/1993  European Pat. Off. .
97/19679  6/1997  WIPO .

OTHER PUBLICATIONS

Das et al., *Journal of Biological Chemistry*, 267(27), 19172–19178(1992).
Domany et al., *Pharmazie*, 49, 807–810 (1994).
Shibuya et al., *Hepatology*, 25(2), 356–360 (1997).
Wang et al., *Hepatology*, 15(6), 1112–1116 (1992).
Engels et al., *FEBS Letters*, 305(3), 254–256 (1992).
Pearse et al., *Am. J. Respir. Crit. Care Med.*, 153, 196–202 (1996).
t'Hart et al., *Biotech Therapeutics*, 3(3 and 4), 119–135 (1992).

*Primary Examiner*—Raymond Henley, III
*Attorney, Agent, or Firm*—Leydig, Voit & Mayer, Ltd.

[57] ABSTRACT

The present invention is directed to a method for the prophylactic and therapeutic treatment of reperfusion injury or injury due to a distal reperfusion. The method involves the administration of an NADPH-oxidase inhibitor to a cell, tissue, organ or animal in an amount sufficient to treat the cell, tissue, organ or animal for reperfusion injury prophylactically or therapeutically. The NADPH-oxidase inhibitor preferably is an o-methoxycatechol, or a pharmaceutically acceptable salt, derivative, dimer or prodrug thereof. Most preferably, the o-methoxycatechol is apocynin.

10 Claims, No Drawings

USE OF AN NADPH-OXIDASE INHIBITOR IN THE TREATMENT OF REPERFUSION INJURY

This application claims priority to U.S. provisional patent application Ser. Nos. 60/058,446, filed Sep. 10, 1997, and 60/071,188, filed Jan. 12, 1998.

TECHNICAL FIELD OF THE INVENTION

The present invention relates to a method for the prophylactic and therapeutic treatment of reperfusion injury, such as that resulting from ischemia or hypoxia.

BACKGROUND OF THE INVENTION

"Reperfusion" refers to the re-establishment of blood flow to a cell, a tissue or an organ after a period of time in which blood flow to the same collection of cells, tissue or organ was partially or completely interrupted, i.e., "ischemia." Reperfusion also refers to the flow of "normoxic" blood, i.e., blood in which the oxygen content is sufficient to satisfy normal cellular oxygen requirements, to a collection of cells, a tissue or an organ after a period of time in which "hypoxic" blood, i.e., blood in which the oxygen content is insufficient to satisfy normal cellular oxygen requirements, was flowing to the same collection of cells, tissue or organ.

Reperfusion is often associated with a number of diseases and conditions/events as well as a number of medical procedures. It is most commonly associated with stroke, heart attack, cardiac surgery, in particular cardiac surgery involving cardiopulmonary bypass, and transplantation of cells, a tissue or an organ.

Reperfusion often results in injury—thus, the term "reperfusion injury." Reperfusion injury can run the gamut from subcellular damage to gross cellular damage. For example, reperfusion can result in the disruption of nucleic acid sequencing, the destruction of cell membrane integrity, the failure of normally tight intercellular junctions, as well as hemorrhage and edema.

The exact cascade of events initiated by reperfusion and leading to injury is unclear. It is likely that the cascade of events, which involves the release of multiple cellular products, including thromboxanes, components of complement, such as C3a and C5a, and free radicals, leads to unbridled destruction by the normally selective and contained defense system of the body. Central to this defense system is the NADPH-oxidase enzyme, which was first characterized in leukocytes but now has been identified in multiple other types of cells and tissues, including monocytes, smooth muscle cells, endothelial cells, the carotid body and lung tissue.

The NADPH-oxidase enzyme is a complex of membrane-bound and cytosolic components. The complex is unassembled, i.e., inactive, in quiescent cells. Upon cell perturbation, e.g., by infection, however, the membrane-bound and cytosolic components assemble to form the active complex. The membrane-bound component includes cytochrome b558, which consists of a 22 kD protein (p22$_{[phox]}$) bound tightly to a 91 kD glycosylated integral membrane protein (gp91$_{[phox]}$). The cytosolic component comprises a 47 kD protein (p46$_{[phox]}$), a 67 kD protein (p67$_{[phox]}$), and a low molecular weight GTP-binding protein.

NADPH-oxidase transfers electrons from NADPH to oxygen, resulting in the generation of reactive oxygen species, such as $O_2^-$ and $H_2O_2$, in an intense process referred to as "oxidative burst." Under normal conditions, the reactive oxygen species generated by NADPH-oxidase are part of the body's defense system against, for example, microorganisms. However, during reperfusion, NADPH-oxidase can play a role in cellular destruction.

Four-hydroxy-3-methoxyacetophenone, commonly referred to as "apocynin," is a known inhibitor of NADPH-oxidase. It is a compound that has been isolated from the root of the plant *Picrorhiza kurroa*, which grows in the Himalayan mountains. Extracts of *Picrorhiza kurroa* have been used in acute and chronic preparations, given topically, systemically, intravascularly or orally, to treat inflammatory diseases, arthritis, sepsis-related lung injury, liver disease, lung disease, fever, skin lesions, wound infections, rheumatic disease, urinary disorders, heart failure, and snake and scorpion bites. It has been disclosed as useful in the treatment of acute and chronic inflammations of the airways, joints and blood vessels (EP 551662). It also has been disclosed as useful in the treatment of a metabolic condition, namely atherosclerosis (WO 97/19679). It also has been suggested to be useful in the prevention of thrombosis (Engels et al., *FEBS Letter* 305: 254–256 (1992)).

It now has been surprisingly and unexpectedly discovered that inhibitors of NADPH-oxidase, such as apocynin, are useful in the prophylactic and therapeutic treatment of reperfusion injury. Accordingly, it is a principal object of the present invention to provide a method of prophylactically and therapeutically treating reperfusion injury, such as that resulting from ischemia or hypoxia. This and other objects of the present invention will become apparent from the detailed description provided herein.

BRIEF SUMMARY OF THE INVENTION

The present invention is directed to a method for the prophylactic and therapeutic treatment of reperfusion injury. The method involves the administration of an NADPH-oxidase inhibitor. Preferably, the NADPH-oxidase inhibitor is a compound of formula:

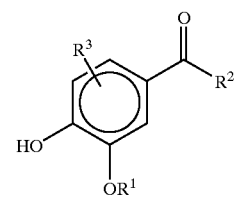

wherein $R^1$, $R^2$, and $R^3$ are independently selected from the group consisting of hydrogen, alkyl, cycloalkyl, heterocycloalkyl, alkenyl, alkynyl, aryl, heteroaryl, arylalkyl, and heteroarylalkyl, each of which may be unsubstituted or substituted. More preferably, the NADPH-oxidase inhibitor is an o-methoxycatechol or an NADPH-oxidase inhibiting pharmaceutically acceptable salt, derivative, dimer or prodrug thereof. Most preferably, the NADPH-oxidase inhibitor is apocynin or an NADPH-oxidase inhibiting pharmaceutically acceptable salt, derivative, dimer or prodrug thereof.

DETAILED DESCRIPTION OF THE INVENTION

The present invention is predicated on the surprising and unexpected discovery that reperfusion injury can be prophylactically and therapeutically treated by administering an inhibitor of NADPH-oxidase.

Accordingly, the present invention provides a method for the prophylactic and therapeutic treatment of a cell, tissue, organ or animal, such as a mammal, in particular a human, for reperfusion injury, such as that resulting from ischemia or hypoxia. By "prophylactic" is meant the protection, in whole or in part, against reperfusion injury. By "therapeutic" is meant the amelioration of reperfusion injury, itself, and the protection, in whole or in part, against further reperfusion injury. In this regard, the present invention also provides a method for the prophylactic and therapeutic treatment of a cell, tissue or organ for injury due to a distal reperfusion. Such injury can result from the distal reperfusion, itself, or from products released from the site of the distal reperfusion.

The method comprises administering to the cell, tissue, organ or animal a compound that inhibits NADPH-oxidase in an amount sufficient to treat the cell, tissue, organ or animal for reperfusion injury or injury due to a distal reperfusion prophylactically or therapeutically. Preferably, the inhibitor of NADPH-oxidase inhibits activation of NADPH-oxidase. By "activation" is meant the change in state of NADPH-oxidase from inactive to active. More preferably, the inhibitor of NADPH-oxidase activation inhibits assembly of functional NADPH-oxidase, such as by conjugation to essential thiol groups of the membrane-bound and/or cytosolic component(s) of NADPH-oxidase. By "assembly" is meant assembly of the membrane-bound and cytosolic components of NADPH-oxidase so as to form an active, functional NADPH-oxidase.

Alternatively, the inhibitor of NADPH-oxidase, more specifically, the inhibitor of NADPH-oxidase activation, and even more specifically, the inhibitor of NADPH-oxidase assembly, can be described as an inhibitor of "oxidative burst"—the intense process by which NADPH-oxidase transfers electrons from NADPH to oxygen, resulting in the generation of reactive oxygen species, such as $O_2^-$ and $H_2O_2$. Accordingly, use of the term "NADPH-oxidase inhibitor" is intended to encompass all of these compounds, including pharmaceutically acceptable salts thereof, derivatives thereof, dimers thereof, and prodrugs thereof, which can be metabolically converted into an inhibitor of NADPH-oxidase or oxidative burst.

Any NADPH-oxidase inhibitor can be used in the method of the present invention as long as it is safe and efficacious. Suitable examples of such compounds include those set forth in WO 97/19679 and t'Hart et al., *Biotechnology Therapeutics* 3 (3 and 4): 119–135 (1992), both of which are specifically incorporated herein in their entireties by reference. Accordingly, the inhibitor of NADPH-oxidase can be a compound of the formula:

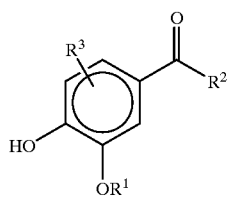

wherein $R^1$, $R^2$, and $R^3$ are independently selected from the group consisting of hydrogen, alkyl, cycloalkyl, heterocycloalkyl, alkenyl, alkynyl, aryl, heteroaryl, arylalkyl, and heteroarylalkyl, each of which may be unsubstituted or substituted. Suitable NADPH-oxidase inhibitors include (i) an o-methoxy catechol, (ii) a pharmaceutically acceptable salt thereof, (iii) a derivative thereof, which inhibits NADPH-oxidase, (iv) a dimer (or tautomer thereof) of an o-methoxy catechol or a derivative thereof, which inhibits NADPH-oxidase, or (v) a prodrug of an o-methoxy catechol, a derivative thereof or a dimer thereof, wherein said prodrug can be metabolically converted into an inhibitor of NADPH-oxidase. Preferably, the NADPH-oxidase inhibitor is apocynin, i.e., 4-hydroxy-3-methoxyacetophenone, which is a compound of the above formula, wherein $R^1$ and $R^2$ are each methyl and $R^3$ is hydrogen, or a pharmaceutically acceptable salt, a derivative, a dimer or a prodrug thereof.

"Alkyl" includes linear and branched alkyl groups, preferably of twenty carbons or less. "Cycloalkyl" includes cyclic alkyl groups and cyclic alkyl groups, which comprise a linear and/or a branched alkyl group, preferably of twenty carbons or less. Preferably, the cycloalkyl comprises a cyclic $C_3$–$C_8$ group.

"Heterocycloalkyl" includes a cyclic alkyl group in which at least one of the methylene groups is replaced by a heteroatom, such as nitrogen or sulfur, which may be unsubstituted or substituted. Examples of heterocycloalkyls include tetrahydrofuranyl, piperidine, dioxanyl and the like.

"Alkenyl" includes a $C_2$–$C_8$ unsaturated hydrocarbon of a linear, branched or cyclic ($C_{5-6}$) configuration and combinations thereof. "Alkynyl" includes a $C_2$–$C_8$ hydrocarbon of a linear or branched configuration and combinations thereof, which comprises at least one triple bond.

"Aryl" and "heteroaryl" include a 5- or 6-membered aromatic or heteroaromatic ring containing one or more heteroatoms, preferably no more than three heteroatoms, which are selected from the group consisting of oxygen, nitrogen and sulfur, a bicyclic 9- or 10-membered aromatic or heteroaromatic ring system containing one or more heteroatoms, preferably no more than three heteroatoms, which are selected from the group consisting of oxygen, nitrogen and sulfur, and a tricyclic 13- or 14-membered aromatic or heteroaromatic ring system containing one or more heteroatoms, preferably no more than three heteroatoms, which are selected from the group consisting of oxygen, nitrogen and sulfur. The aryl and heteroaryl groups can be substituted with one or more groups, preferably no more than three groups, selected from the group consisting of an unsubstituted or a substituted $C_1$–$C_8$ alkyl, an unsubstituted or a substituted alkynyl, =O, —$NO_2$, halo, hydroxy, alkoxy, —$OCH(COOH)_2$, cyano, —$NR_4R_4$ (wherein $R_4$ is independently selected from the group consisting of hydrogen, $C_1$–$C_8$ alkyl and cycloalkyl, or $R_4R_4$, together with the nitrogen atom, can form a cyclic ring), acylamino, phenyl, benzyl, phenoxy, benzyloxy, heteroaryl and heteroaryloxy, wherein each of said phenyl, benzyl, phenoxy, benzyloxy, heteroaryl and heteroaryloxy is optionally substituted with one or more groups, preferably no more than three groups, which are selected from the group consisting of $C_1$–$C_8$ alkyl, alkenyl, alkynyl, halo, hydroxyl, alkoxy, cyano, phenyl, benzyl, benzyloxy, carboxamido, heteroaryl, heteroaryloxy, —$NO_2$, and —$NR_4R_4$. The aromatic 6–14-membered carbocyclic rings include, for example, benzene, naphthalene, benzopyranone, thiazole, furan, benzimidazole, quinoline, isoquinoline, quinoxaline, pyrimidine, pyrazine, tetrazole and pyrazole.

By "alkoxy" is meant a $C_1$–$C_8$ group that is straight, branched, cyclic or a combination thereof. By "acylamino" is meant a $C_1$–$C_8$ group that is straight, branched, cyclic or a combination thereof. "Halo" includes fluorine, chlorine, bromine and iodine. Alkyl, cycloalkyl, heterocycloalkyl, alkenyl and alkynyl can be substituted with one or more groups, preferably no more than three groups, which are selected from the group consisting of halo, hydroxy, a lower alkoxy, preferably of twenty carbons or less, carboxy, carboalkoxy, carboxamido, cyano, carbonyl, $NO_2$, $NR_5R_5$ (wherein $R_5$ is hydrogen, alkyl or arylalkyl), alkylthio, sulfoxide, sulfone, acylamino, amidino, phenyl, benzyl, heteroaryl, phenoxy, benzyloxy, and heteroaryloxy, wherein phenyl, benzyl, heteroaryl, phenoxy, benzyloxy and heteroaryloxy can be substituted as well.

Compounds of the above formula are widely available commercially. Those that are not commercially available can be prepared by Friedel-Crafts acylation of the appropriate phenol or protected phenol, by aryllithium addition of a protected phenol to the appropriate carboxylic acid or by arylcadmium addition to an acid chloride, followed by deprotection, or by ketone synthesis methods known to those of ordinary skill in the art. Dimers can be made by oxidative dimerization of the appropriate phenol. Oxidation to the quinoid compound can be done by using any convenient oxidant, such as hydrogen peroxide.

Whether or not a particular derivative of apocynin can inhibit NADPH-oxidase can be determined by its effect upon oxygen consumption, NADPH oxidation or radical production, such as production of superoxide, in an assay similar to one of the following assays. Oxygen consumption can be assayed by quantifying changes in oxygen content in a closed system. A decrease in oxygen content represents oxygen utilization by the oxidase system for the production of oxygen free radicals.

Thus, an apocynin derivative of interest can be combined with a soluble neutrophil fraction (50–150 $\mu$l) and a membrane neutrophil fraction (25–50 $\mu$l; equivalent of 2–4×10$^6$ neutrophils purified by centrifugation on a discontinuous sucrose gradient) and assay buffer (10 mM Hepes/10 mM potassium phosphate; 0.17 M sucrose; 175 mM NaCl; 0.5 mM EGTA; 1 mM $MgCl_2$, 10 $\mu$m GTP-γ-S, pH 7.0) at 27° C. Then, 25–100 $\mu$l of sodium dodecyl sulfate (SDS) are added to a final concentration of 100 $\mu$M. The reaction mixture is incubated for 4 min and NADPH is added to a final concentration of 200 $\mu$M and the oxygen consumption is recorded at 27° C. using a Clarke electrode. Oxygen consumption indicates assembly and activation of the NADPH oxidase complex. Arachidonic acid, at concentrations determined by the concentrations of the soluble and membrane fractions utilized, can be substituted for SDS. Examples of such assays include those described by t'Hart et al. (*Free Radical Biol. Med.* 8: 241–249 (1990)), Bolscher et al. (*J. Clin. Invest.* 83: 753–763 (1989)), Curnette et al. (*J. Biol. Chem.* 262: 5563–5569 (1987)), Pilloud et al. (*Biochem. Biophys. Res. Comm.* 159(2): 783–790 (1989)) and Doussiere et al. (*Biochem. Biophys. Res. Comm.* 152(3): 993–1001 (1988)).

NADPH oxidation can be assayed by monitoring some aspect of the oxidase that is known to undergo a characteristic change upon oxidation. Observation of the characteristic change represents oxidation of NADPH. Typically, this involves spectroscopic evaluation of light absorption at various wavelengths (366 nm for NADPH, 580–530 nm for cytochrome b 588, and 450–500 nm for flavin oxidoreduction) characteristic of the oxidized or reduced form of a component of the enzyme. Resonance Raman spectroscopies, fluorometric markers of oxidation or absorption decrease at nonoxidized wavelengths as proxy for the rate of oxidation also can be used. Examples of such assays include those described by Koshkin et al. (*Biochim. Biophys. Acta* 1319: 139–146 (1997)), Cross et al. (*Biochem. J.* 194: 363–367 (1981); *J. Biol. Chem.* 270(14): 8194–8200 (1995); *J. Biol. Chem.* 270(29): 17075–17077 (1995), Escriou et al. (*Eur. J. Biochem.* 245(2): 505–511 (1997)), and Winston et al. (*Arch. Biochem. Biophys.* 304(2): 371–378 (1993)).

Radical production can be assayed by monitoring the production of superoxide radicals by activated NADPH oxidase in the presence of oxygen and other cofactors. The production of superoxide radicals is proportional to the degree of enzyme activation. Numerous detection and quantification methods are available and include the use of fluorescence, chemiluminescence, electron paramagnetic resonance and spectrophotometric reduction of a marker compound. Examples of such assays include those described by Morel et al. (*Biochim. Biophys. Acta* 1182: 101–109 (1993)) and O'Donnell et al. (*Biochem. J.* 290: 41–49 (1993)).

Whether or not a particular prodrug of apocynin can be metabolically converted into an NADPH-oxidase inhibitor can be determined in any one of a number of ways. One basic approach is to expose a compound to the various chemical and/or enzymatic milieus to which it will be exposed in the body and to determine whether or not the exposure activates the compound. Then, the ability of the prodrug to inhibit NADPH-oxidase can be evaluated in the presence and absence of the chemical/enzymatic milieu. If the prodrug inhibits NADPH-oxidase in the presence of the milieu but not in the absence of the milieu, then the prodrug must be converted into an NADPH-oxidase inhibitor in the presence of the milieu. The NADPH-oxidase inhibiting effect of the prodrug then can be assayed as described above.

In this regard, one of ordinary skill in the art will appreciate that prodrugs only can be used in those situations where metabolic conversion to an NADPH-oxidase inhibitor is possible. For example, in the presence of myeloperoxidase and products released by activated neutrophils, o-methoxycatechols can be oxidized to quinone-methide or demethoxylated to orthoquinone. Quinone-methide and orthoquinone are capable of conjugating thiol groups, such as those which are present on the membrane-bound and/or cytosolic components of NADPH-oxidase (or thiol-containing compounds involved in the synthesis of such components). Conjugation of such thiol groups inhibits assembly of functional NADPH-oxidase. This can lead to rapid deactivation of NADPH-oxidase in intact neutrophils, thereby inhibiting rapid turnover of NADPH-oxidase, which is essential to sustained superoxide generation. In contrast, such metabolic conversion probably would not occur where the compound is being used in a storage solution of an organ to be transplanted.

The NADPH-oxidase inhibitor can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable.

An advantage of the compounds used in the present inventive method is that, in contrast to neutrophil depleting agents, they are safe when given systemically, even for weeks or months. In contrast to free radical scavenging agents, they do not result in the production of potentially dangerous compounds, such as hydrogen peroxide, a byproduct of superoxide dismutase action (SOD). Furthermore, in contrast to agents that increase intracellular cyclic AMP (cAMP), the compounds completely block reperfusion injury to the lung without activating ubiquitous signal transduction systems, which could subject the recipient to deleterious side effects.

The method for the prophylactic and therapeutic treatment of reperfusion injury is useful in the treatment of any and all reperfusion injuries to a cell, a tissue or an organ, whether in vitro, such as for purposes of transplantation or research, or in vivo, including, but not limited to, reperfusion injuries due to ischemia or hypoxia. In this regard, it is important to note that reperfusion injury can result, for example, from the (i) direct exposure of a given cell, tissue, organ or organism to reperfusion injury-inducing condition(s), such as ischemia (e.g., change in blood flow) or hypoxia (e.g., change in oxygen tension), (ii) the indirect exposure of a given cell, tissue, organ or organism to reperfusion injury-inducing condition(s), such as exposure to another cell, tissue or organ or a product(s) of another cell, tissue or organ exposed to reperfusion-injury inducing condition(s), such as ischemia or hypoxia, or (iii) a combination of both direct and indirect exposure. The method is especially useful in the treatment of an animal, in particular a mammal, specifically a human, in particular with respect to reperfusion injury of a lung, a heart, a liver, an intestine, a pancreas, a kidney, a limb or the brain, for example.

In view of the above, the method is useful in the prophylactic and therapeutic treatment of reperfusion injury associated with reperfusion-stimulated neutrophil activation, such as that associated with a surgical procedure, e.g., cardiopulmonary bypass, which involves pulmonary, cardiac and vascular dysfunction, cell/tissue/organ transplantation, such as orthotopic lung transplant, pulmonary embolus, thoracic surgery involving prolonged compression of the lung, stroke, trauma, seizure, myocardial infarction, angioplasty, ischemic bowel syndrome, ulcers, skin and muscle flaps (such as those generated during injury or surgery), hypothermia, e.g., frostbite, reattachment of a body part, and neutrophil-activation associated damage of lung, liver and kidney associated with distal ischemia reperfusion injury, among others.

With respect to transplantation, for example, an NADPH-oxidase inhibitor can be administered to a donor prior to removal of cells, a tissue or an organ so as to attain therapeutic levels of the compound in the donor (specifically, the donor organ) by the time the cells, tissue or organ (kidney, heart, lung, liver and pancreas; etc.) is/are removed from the donor for transplantation. Following removal of the cells, tissue or organ, and prior to transplantation of the same into a recipient, the donor cells, tissue or organ can be treated (e.g., "flushed") with an NADPH-oxidase inhibitor, such as apocynin (or its salt, derivative or dimer) in a pharmaceutically acceptable excipient. Similarly, the recipient can be treated before, during or after transplantation with an NADPH-oxidase inhibitor, such as apocynin or its salt, derivative, dimer or prodrug, in a pharmaceutically acceptable excipient.

The NADPH-oxidase inhibitor is preferably administered as soon as possible after it has been determined that a cell, a collection of cells, a tissue, an organ or an organism, in particular an animal, such as a mammal, specifically a human, is at immediate risk for reperfusion injury or has just begun to realize reperfusion injury. It is expected that, in most situations, the NADPH-oxidase inhibitor will be administered within about 15 min to about 60 min of injury, i.e., before or after injury as appropriate. When it is possible to predict the onset of reperfusion, e.g., such as that associated with transplantation, the NADPH-oxidase inhibitor should be administered immediately upon knowledge of need. When reperfusion injury has already begun, the NADPH-oxidase inhibitor should be administered as soon as possible after the onset of reperfusion. Treatment will depend, in part, upon the particular NADPH-oxidase inhibitor used, the amount of the NADPH-oxidase inhibitor administered, the route of administration, and the cause and extent of reperfusion injury realized.

One skilled in the art will appreciate that suitable methods of administering an NADPH-oxidase inhibitor useful in the method of the present invention are available. Although more than one route can be used to administer a particular NADPH-oxidase inhibitor, a particular route can provide a more immediate and more effective reaction than another route. Accordingly, the described methods are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors including the strength of the particular NADPH-oxidase inhibitor employed, the age, species, condition or disease state, and body weight of the animal, as well as the amount of cells or tissue or organ about to be affected or actually affected by reperfusion injury. The size of the dose also will be determined by the route, timing and frequency of administration as well as the existence, nature, and extent of any adverse side-effects that might accompany the administration of a particular NADPH-oxidase inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.001 to about 1000 mg, preferably about 0.01 to about 100 mg, of one or more of the compounds or polymers described above per kg treated weight, i.e., weight of treated cells, tissue, organ or animal.

Compositions for use in the present inventive method preferably comprise a Pharmaceutically acceptable carrier and an amount of an NADPH-oxidase inhibitor sufficient to treat reperfusion injury prophylactically or therapeutically. The carrier can be any of those conventionally used and is limited only by chemico-physical considerations, such as solubility and lack of reactivity with the compound, and by the route of administration. It will be appreciated by one of skill in the art that, in addition to the following described pharmaceutical composition, the NADPH-oxidase inhibitor can be formulated as inclusion complexes, such as cyclodextrin inclusion complexes, or liposomes.

The NADPH-oxidase inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the NADPH-oxidase inhibitor and one which has no detrimental side effects or toxicity under the conditions of use.

The choice of excipient will be determined in part by the particular NADPH-oxidase inhibitor, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Injectable formulations are among those formulations that are preferred in accordance with the present inventive method. The requirements for effective pharmaceutical carriers for injectable compositions are well known to those of ordinary skill in the art (See *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986)). It is preferred that such injectable compositions be administered intravenously or locally, i.e., at or near the site of reperfusion injury.

Topical formulations are well-known to those of skill in the art and are suitable in the context of the present invention for application to skin.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The NADPH-oxidase inhibitors used in the present inventive method, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer. Such spray formulations may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds and polymers useful in the present inventive method can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The present inventive method also can involve the co-administration of other pharmaceutically active compounds. By "co-administration" is meant administration before, concurrently with, or after administration of an NADPH-oxidase inhibitor as described above. For example, neutrophil-specific antibodies, such as anti-CD-18, and/or other agents that block neutrophil adhesion, such as NPC 15669, agents that induce neutropenia, such as cyclophosphamide, neutrophil inhibitors, such as recombinant neutrophil inhibitory factor, lodoxamide tromethamine and beraprost, neutrophil elastase inhibitors, such as ONO-5046, PAF antagonists, such as TCV-309, and hemorheological agents that alter neutrophil function, such as ReothRx (poloxamer 188 NF), can be administered, in particular where reperfusion involves high levels of neutrophil infiltration. Other compounds, such as xanthine oxidase inhibitors, e.g., allopurinol and oxypurinol, nitric oxide synthase inhibitors, such as $N^G$-nitro-L-arginine-methyl-ester (L-NAME), anti-oxidants, free-radical scavengers, e.g., superoxide dismutase, catalase and nicaraven, ibuprofen, superoxide dismutase, polyethylene glycol-conjugated superoxide dismutase, diethylthiourea with diltiazem and amiloride/dimethylamiloride, pentoxifylline, propentofylline, and 21-aminosteroids also can be administered. Adjuvants to thrombolytic agents, such as a neutrophil elastase inhibitor, e.g., ICI 200,000, can be co-administered, for example, for myocardial infarction. A metalloprotein superoxide dismutase mimic can be administered with respect to ischemia reperfusion, in general.

EXAMPLES

The following examples further illustrate the present invention, but, of course, should not be construed as in any way limiting its scope.

Example 1

This example demonstrates the efficacy of apocynin in the treatment of ischemia reperfusion-induced lung injury in sheep.

Apocynin, which is commercially available as a water-soluble powder, was administered to sheep in accordance with an extremely sensitive model for the evaluation of ischemia reperfusion-induced lung injury (Pearse et al., Am. J. Respir. Crit. Care Med. 153: 196–202 (1996)). In this in situ isolated lung preparation, which has been approved by the Johns Hopkins Committee on Animal Research, sheep were anesthetized with atropine (intramuscular) and ketamine (intramuscular and intravenous) and ventilated with oxygen- and $CO_2$-supplemented room air (inspired oxygen 28%, inspired $CO_2$ 5%) via tracheostomy. The sheep were exsanguinated via a left atrial catheter, and the pulmonary artery and left atrium were cannulated for connection to an extracorporeal circuit. In the ischemia-reperfusion group, blood flow to the lungs was arrested for a 30-min ischemic period, and the lungs were reperfused for 180 min using a mixture of autologous blood and 3% dextran in Ringers lactate solution.

Following the reperfusion period, the lungs were excised and evaluated for reperfusion-induced lung injury by gross examination, lung water determination, and determination of vascular permeability as measured by reflection coefficient. The reflection coefficient is a highly sensitive index of vascular protein permeability. Reflection coefficient values close to 1.0 indicate healthy pulmonary vessels, which are nearly impermeable to protein molecules, whereas values close to zero indicate injured, leaky blood vessels, which are very permeable to protein.

Apocynin (3 mM) was administered 15 minutes prior to ischemia as a single injection into the pulmonary artery, as well as continuously throughout the 180-min reperfusion period by addition of apocynin to the perfusate. These lungs were compared to an ischemic-perfused (IR) control group, which was treated with the same volume of drug diluent (0.9% saline). An additional group of untreated, rapidly excised unperfused lungs was also studied to determine uninjured normal values.

The results, which are in the following table as means ± SE, demonstrate that apocynin completely prevents the increased vascular protein permeability and hemorrhage caused by this injury and markedly attenuates the increased lung water.

|  | Apocynin-treated IR (n = 5) | Control IR (n = 3) | Nonperfused Control (n = 5) |
|---|---|---|---|
| Reflection Coefficient | 0.93 ± 0.03 | 0.56 ± 0.04* | 0.74 ± 0.03 |
| Lung Blood (g/g bld-free dry wt) | 2.07 ± 0.15 | 7.72 ± 6.15* | 2.12 ± 0.16 |
| Lung Water (g/g bld-free dry wt) | 5.58 ± 0.04 | 7.77 ± 0.35* | 4.80 ± 0.23 |

$p < 0.05$ vs. apocynin-treated IR and nonperfused control

The control IR lungs have a significantly lower reflection coefficient and greater amounts of both lung blood and water than the nonperfused control lungs, indicating marked lung injury. Using the nonperfused group as an estimate of normal, apocynin treatment completely prevented the decrease in reflection coefficient and the increase in lung hemorrhage and blunted the increase in lung water. The reflection coefficient, the most sensitive and specific indicator of lung injury, was actually greater in the apocynin-treated IR lungs than in the nonperfused controls, which indicates that the apocynin-treated IR lungs were more healthy, i.e., less permeable to protein molecules, than untreated lungs.

Example 2

This example demonstrates the dose response of apocynin in ischemia reperfusion injury of the lung.

Seventeen sheep lungs were subjected to 30 min of ischemia and 180 min of reperfusion with autologous blood. Either diluent or 3 mM, 0.3 mM or 0.03 mM apocynin (APO) was administered to the pulmonary artery early in ischemia and the reservoir before perfusion. Following reperfusion (IR), the lungs were excised and subjected to increased static vascular pressures to measure the reflection coefficient for albumin ($\sigma_{alb}$) and the filtration coefficient (Kf) as well as extravascular lung water (EVLW). A group of nonreperfused lungs (Nonreper.) served as an estimate of normal lung fluid balance. The results are as shown in the table below ($p<0.05$ vs. diluent ischemia-reperfusion).

| Group | n | $\alpha_{alb}$ | Kf (g/min/mmHg/100 g) | EVLW (g/g bfdw) |
|---|---|---|---|---|
| Nonreper. | 5 | 0.74 ± 0.03* | 0.033 ± 0.021* | 4.79 ± 0.23* |
| 3 mM APO + IR | 5 | 0.93 ± 0.03* | 0.058 ± 0.17 | 5.43 ± 0.42* |
| 0.3 mM APO + IR | 4 | 0.68 ± 0.08 | 0.08 ± 0.01 | 6.30 ± 0.55 |

| Group | n | $\alpha_{alb}$ | Kf (g/min/mmHg/100 g) | EVLW (g/g bfdw) |
|---|---|---|---|---|
| 0.03 mM APO + IR | 3 | 0.46 ± 0.09 | 0.17 ± 0.08 | 10.9 ± 5.53 |
| Diluent + IR | 5 | 0.47 ± 0.11 | 0.16 ± 0.07 | 7.99 ± 0.29 |

*p < 0.05 vs. diluent ischemia-reperfusion

Apocynin at 3 mM completely prevented the decrease in $\sigma_{alb}$ and the increase in EVLW caused by ischemia reperfusion injury, suggesting that NADPH oxidase contributes significantly to ischemia reperfusion injury in isolated sheep lungs.

Example 3

This example demonstrates the efficacy of apocynin in the treatment of ischemia reperfusion associated with cardiopulmonary bypass in sheep.

Sheep received either diluent or apocynin to produce a calculated blood concentration of 3 mM 15 min prior to cardiopulmonary bypass. The sheep were then subjected to 2 hr of warm cardiopulmonary bypass. The sheep were then followed for 1 hr after separation from cardiopulmonary bypass.

The sheep pretreated with apocynin demonstrated more efficient oxygen loading and carbon dioxide removal then the untreated sheep. Excised lungs also showed less gross hemorrhage and less measurable blood extravasation to the interstitial space.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of prophylactically or therapeutically treating a cell, a tissue, an organ or an animal, for reperfusion injury, which method comprises administering to said cell, tissue, organ or organism an NADPH-oxidase inhibitor in an amount sufficient to treat said cell, tissue, organ or animal for reperfusion injury prophylactically or therapeutically.

2. The method of claim 1, wherein said NADPH-oxidase inhibitor is a compound of formula:

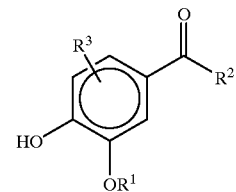

wherein $R^1$, $R^2$, and $R^3$ are independently selected from the group consisting of hydrogen, alkyl, cycloalkyl, heterocycloalkyl, alkenyl, alkynyl, aryl, heteroaryl, arylalkyl, and heteroarylalkyl, each of which may be unsubstituted or substituted.

3. The method of claim 2, wherein said NADPH-oxidase inhibitor is an o-methoxycatechol or an NADPH-oxidase-inhibiting pharmaceutically acceptable salt, derivative, dimer or prodrug thereof.

4. The method of claim 3, wherein said NADPH-oxidase inhibitor is apocynin or an NADPH-oxidase-inhibiting pharmaceutically acceptable salt, derivative, dimer or prodrug thereof.

5. The method of claim 1, wherein said reperfusion injury is that which is associated with a surgical procedure.

6. The method of claim 5, wherein said surgical procedure is cardiac surgery involving cardiopulmonary bypass.

7. The method of claim 5, wherein said surgical procedure is transplantation of cells, a tissue or an organ.

8. The method of claim 7, wherein said NADPH-oxidase inhibitor is administered to (i) a transplant donor prior to removal of said cells, tissue or organ, (ii) a transplant recipient before, during or after transplantation, and (iii) said cells, tissue or organ after removal from the transplant donor and prior to transplantation into the transplant recipient.

9. The method of claim 1, wherein said NADPH-oxidase inhibitor is administered to a lung, a heart, a liver, an intestine, a pancreas, a kidney, a brain or a limb of an animal.

10. A method of prophylactically or therapeutically treating a cell, a tissue or an organ for an injury due to a distal reperfusion, which method comprises administering to said cell, tissue or organ an NADPH-oxidase inhibitor in an amount sufficient to treat said cell, tissue or organ for an injury due to a distal reperfusion prophylactically or therapeutically.

* * * * *